United States Patent [19]

Ams et al.

[11] Patent Number: 5,046,510

[45] Date of Patent: Sep. 10, 1991

[54] APPARATUS FOR MEASURING THE THROUGHFLOW OF A BODY LIQUID

[75] Inventors: Felix Ams, Kämpfelbach; Manfred Baier, Knittlingen; Roland Schäfer, Bretten-Dürrenbüchig, all of Fed. Rep. of Germany

[73] Assignee: Richard Wolf GmbH, Knittlingen, Fed. Rep. of Germany

[21] Appl. No.: 547,727

[22] Filed: Jul. 3, 1990

[30] Foreign Application Priority Data

Aug. 11, 1989 [DE] Fed. Rep. of Germany ....... 3926630

[51] Int. Cl.⁵ .............................................. A61B 5/00
[52] U.S. Cl. .................................. 128/771; 73/861.08
[58] Field of Search ............................. 128/760, 771; 73/861.08, 861.35, 864.34

[56] References Cited

U.S. PATENT DOCUMENTS

| | | | |
|---|---|---|---|
| 3,754,220 | 8/1973 | Sztamler et al. | 128/771 |
| 3,820,392 | 6/1974 | Beck et al. | 73/861.08 |
| 4,051,431 | 9/1977 | Wurster | 324/61 |
| 4,484,582 | 11/1984 | Rottenberg et al. | 73/861.08 |
| 4,770,187 | 9/1988 | Lash et al. | 128/760 |
| 4,819,993 | 1/1990 | Barker | 73/861.08 |

FOREIGN PATENT DOCUMENTS 2500094 3/1979 Fed. Rep. of Germany .

Primary Examiner—Max Hindenburg
Attorney, Agent, or Firm—Panitch Schwarze Jacobs & Nadel

[57] ABSTRACT

An apparatus is disclosed for measuring the throughflow of a body liquid, in particular an apparatus for measuring the flow of urine in urological function diagnostics. The apparatus comprises a collecting funnel connected to a tube, which can be suspended in a WC bowl. In the tube are two axially spaced transducers one for continuously determining the electrical conductivity of fluid flowing through the tube from the funnel and the other for determining the specific electrical conductivity of the liquid. An electronic evaluation system determines the throughflow of the liquid upon the basis of the values determined by the transducers.

11 Claims, 1 Drawing Sheet

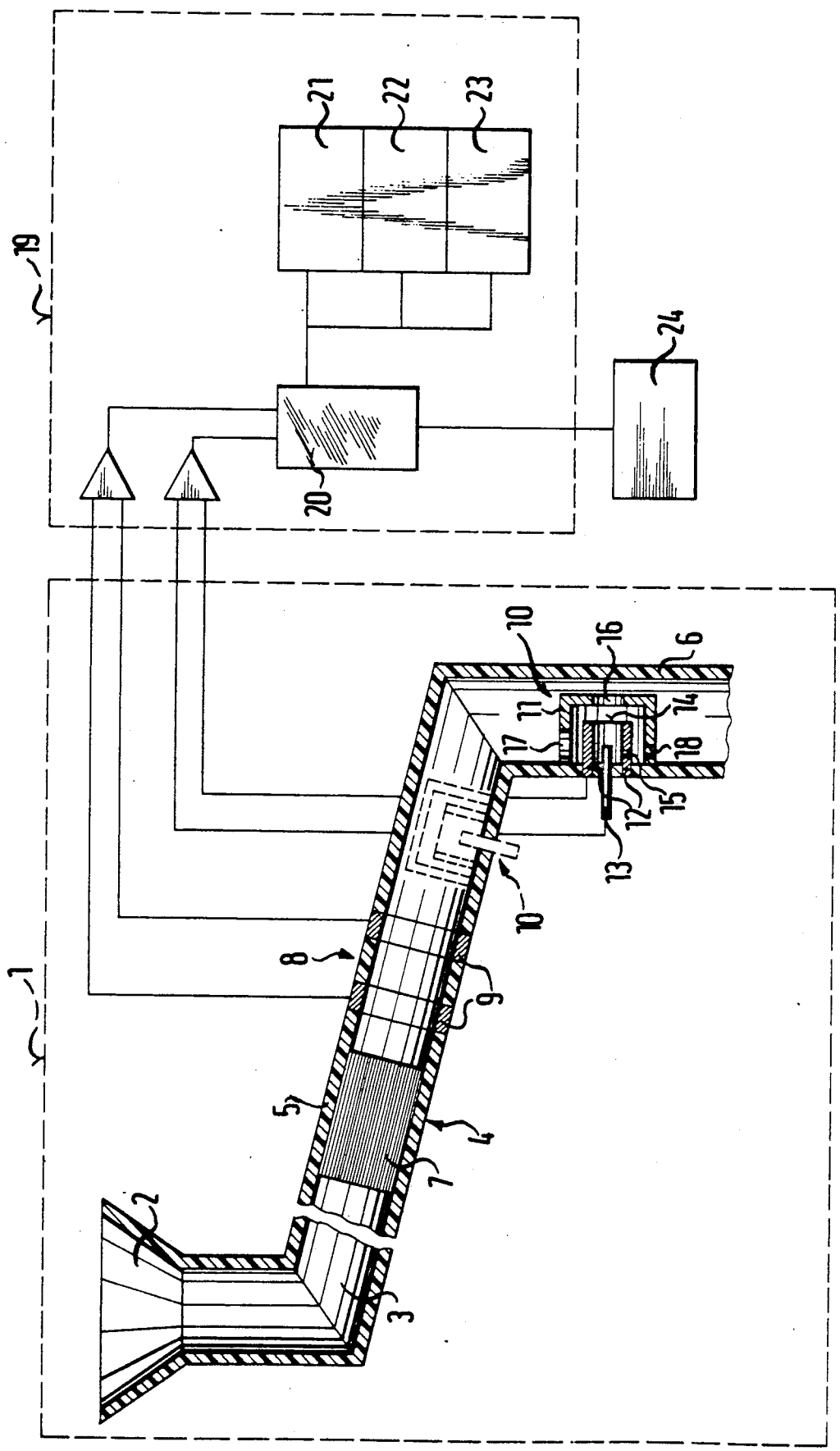

APPARATUS FOR MEASURING THE THROUGHFLOW OF A BODY LIQUID

FIELD OF THE INVENTION

The invention relates to apparatus for measuring the throughflow of a body liquid, in particular for measuring the flow of urine in urological function diagnostics, the apparatus comprising a vessel for collecting the liquid and means for measuring the electrical conductivity thereof.

BACKGROUND OF THE INVENTION

In urological function diagnostics, it is often necessary to measure the flow of a patient's urine (uronecessar flowmetry), in order to determine by the analysis of a uroflowmetry curve, the extent of a micturition disorder. For producing such a curve there is needed a measuring instrument capable of supplying a sufficiently accurate, continuous and reproducible recording of the measured flow values.

Urine flow and micturition volume can be measured, for example, by gravimetry, rotation dynamics, or electrical capacitance or inductance. In gravimetry the weight of the micturition volume is measured and to this end, the urine passed during micturition is collected in a graduated cylinder and weight gains thereof are continuously measured and recorded.

In the rotation dynamics method, the urine stream strikes a disk rotated by a driving motor about vertical axis, thereby causing the disk to be braked. An electronic control unit ensures that the speed of rotation of the disk remains constant and the electric power consumed by the driving motor provides an indication of the quantity of urine striking the disk and hence an indication of the urine flow. The urine is accelerated on the disk and is finally flung against the wall of a housing which serves as a collecting vessel.

Inductive throughflow measurement uses the effect of a magnetic field upon moving matter. Urine, an electric conductor, is moved in the magnetic field, so that an electric voltage is induced in the urine. This induced voltage is, for liquids, proportional to the mean flow rate thereof. In order to measure the throughflow, two electrodes are mounted at right angles to the magnetic field in an electrically non-conductive section of the tube, the induced voltage is measured at these electrodes.

In the case of capacitive uroflowmeters, for example according to the teaching of DE-B 25 00 094, U.S. Pat. No. 4,051,431) a fluid level measurement is converted into a change in capacitance. To this end, a generally cylindrical electrical capacitor is mounted in a collecting vessel for the urine to be measured. The capacitance of this arrangement varies with the level to which the vessel is filled and is therefore a measure of the filling level in relation to time and thus of the volume function, from which the flow of urine can be determined by means of electrical differentiation.

There is described in DE-A-23 30 033, an arrangement in which the electrolytic conductivity of the urine in a collecting vessel is used to measure the fluid level. An uninsulated electrical resistor is partially shunted out or short-circuited relative to an external electrode by the urine. The resistance of said resistor therefore, varies with the height of the fluid level in the vessel and is accordingly a measure of the level to which the vessel is filled.

A disadvantage of most uroflowmeters operating on electrical principles is that each time such a device has been used it must be emptied and cleaned, a laborious process which may give rise to sources of error. Where the resistance of an electrical resistor is measured, as described above, the turns thereof may, for example, be short-circuited by urinary crystals, so that measuring errors can arise, or conductive coatings may form between the test electrodes. Uroflowmeters operating on the principle of rotation dynamics, have apart from cleaning problems, the further disadvantage of being relatively expensive, since a driving motor for the disk and a bearing system therefore, must be provided. In inductive throughflow meters, the measuring signal is relatively small and the electromagnet which is necessarily powerful is relatively expensive.

SUMMARY OF THE INVENTION

The present invention is therefore intended to provide a throughflow meter which is operationally reliable, measures the throughflow accurately, and which can be cleaned without being dismantled.

According to the present invention, therefore, the measuring apparatus comprises a tube, which may be suspended in a WC bowl, and is connected at one end to an open-base liquid collecting vessel, the tube being open at its other end. The tube has therein a first transducer for continuously determining the electrical conductivity of the liquid flowing through the tube and, downstream of said first transducer, a second transducer for determining the specific electrical conductivity of the liquid, an electronic evaluation system for the transducer being provided for determining the throughflow of the liquid.

There is no need to empty the measuring apparatus since the liquid flows therethrough and after each use the apparatus can be cleaned simply by flushing, so that crystals are not deposited therein.

The first transducer may comprise two annular electrodes having inner surfaces flush with the surface of the inner wall of the tube, the electrodes being spaced from one another axially thereof. The second transducer, may comprise a measuring chamber within which is disposed a cylindrical ring electrode, a pin-type electrode, being disposed centrally within the ring electrode. The tube may have an inclined portion connected to the collecting vessel which may be in the form of a funnel, the tube merging into an end portion set at an angle with respect to the inclined portion, the first transducer being disposed in the inclined portion and the second transducer being disposed in said end portion.

The tube may be provided with a laminating zone disposed upstream of the first transducer and comprising grooves or webs extending axially of the tube. The laminating zone causes the initially turbulent liquid to assume a laminar flow through the first transducer so that the electrical conductivity of the liquid can be accurately measured thereby.

In order to enable the specific electrical conductivity of the liquid to be determined by means of the second transducer, the measuring chamber thereof must be completely full. In order to ensure this, the measuring chamber has a larger inlet opening, a smaller outlet opening and an overflow opening, so that the quantity of liquid flowing through between the two electrodes of the second transducer is constant. The values determined by the transducers are evaluated by the electronic evaluation system which at least comprises a processor, a function memory, a measured-value memory and an offset memory. Each transducer may have its own power supply, thereby achieving decoupling therebetween, for the avoidance of measuring errors arising from coupling resistance.

BRIEF DESCRIPTION OF THE DRAWING

The single Figure is a diagram, partly in block schematic form, of apparatus for measuring and recording the throughflow of urine.

DETAILED DESCRIPTION OF THE INVENTION

Apparatus 1 for measuring and recording the throughflow of urine comprises a urine collecting funnel 2 which opens into an elbow socket 3 which in turn opens into one end of a downwardly inclined portion 5 of a tube 4 made of an electrically non-conductive material, for example polyvinylchloride. The other end of the portion 5 leads into a downwardly directed open ended portion 6 of the tube 4. In the upstream part of the portion 5 is a laminating zone 7 comprising webs or grooves extending axially of the tube 4. Downstream of the zone 7, there is located in the portion 5 a first transducer 8 comprising two annular electrodes 9 flush with the inner and outer walls of the tube 4 and being spaced from each other axially thereof. Fixed in the portion 6 of the tube 4, that is to say being downstream of the transducers 9, is a second transducer 10 comprising a measuring chamber 11 containing a cylindrical ring electrode 12 disposed centrally, in which is a pin-type electrode 13. The measuring chamber 11 is formed with an inlet opening 17, an outlet opening 18 diametrically opposite thereto and being smaller than opening 17, and a lateral overflow opening 16 which is larger than the opening 18. The electrode 12 has a lateral, larger inlet opening 14 and a smaller outlet opening 15.

The transducers 8 and 10, which may have their own discrete power supplies, have their outlets connected to inlets of a processor 20 of an electronic evaluation system 19. The system 19 further comprises a function memory 21, a measured-value memory 22 and an offset value memory 23 all connected to the processor 20. A throughflow printer 24 is also connected to the processor 20, for recording the uroflowmetry statistics.

For use, the apparatus 1 may be nested in a WC bowl, urine passed by a patient during micturition passing through the funnel 2 and the elbow socket 3 into the downwardly inclined portion 5 of the tube 4, where the initially turbulent flow of the urine is converted by virtue of the webs or grooves in the zone 7, into a laminar flow in order to avoid the possibility of such turbulent asymmetrical flow of the urine causing measuring errors to occur in the subsequent measurement of the throughflow. The stream of urine flowing from the zone 7 through the first transducer 8, produces an electrically conductive connection between the electrodes 9, the conductivity of which connection depends upon how the urine is located between the electrodes 9. The continuously measured value of that conductivity is a measure of the urine throughflow. Since, however, the measured value of the said conductivity of the urine is also dependent upon the specific electrical conductivity a second transducer is arranged to determine it. In order to enable the transducer 10 to determine the specific conductivity, the measuring chamber 11 must be completely full of urine, this being ensured because the urine is admitted through the relatively larger inlet opening 17 of the chamber 11 while the same quantity of urine as that admitted to the chamber 11 cannot flow out by way of the relatively smaller outlet opening 18 thereof. Air bubbles and excess urine can escape from the chamber 11 by way of the overflow opening 16 thereof, whereby inclusion of air is prevented from falsifying the measurement of the specific conductivity.

Because of the geometry of the first transducer 8 and the inclination of the portion 5 of the tube 4, the interrelationship between the conductivity and the throughflow is non-linear. This interrelationship is stored, by way of the processor 20, in the function memory 21 of the electronic system 19 and is allowed for by multiplication of the measured conductivity values with the contents of the function memory 21, by means of the processor 20 which also stores the measured values in the measured value memory 22 and the offset values measured by the transducers 8 and 10 in the offset memory 23. The said offset values are determined in each case before using the apparatus 1. That is to say before the transducers 8 and 10 are wetted, so that any electrically conductive coatings which could in time form between the electrodes of the transducers cannot falsify the measurement results. The processor 20 takes account of the offset values in each case by subtracting them from the actual measured values, and also controls the output of build-up time, maximum discharge, average discharge, volume, micturition time and discharge time as well as the throughflow rate, the throughflow being printed out either in numerical form or in the form of a discharge-time curve by the printer 24.

The apparatus may alternatively comprise a plurality of tubes in order to produce a laminar flow of the urine, the diameter of the tubes being as small as possible but large enough to avoid any urine remaining in the tubes.

Alternatively, also, the measuring chamber 11 of the second transducer 10, whilst still having a larger inlet opening 17 and a smaller outlet opening 18, may have an electrode arrangement comprising, for example, of two contact pins instead of the concentric ring electrode 12 and pin-type electrode 13.

The transducer 10 could alternatively be positioned as indicated in broken lines in the drawing.

What is claimed is:

1. Apparatus for measuring the throughflow of a body liquid; the apparatus comprising:
   a vessel for collecting the liquid, the vessel having an open base;
   a tube connected to said open base at one end to receive liquid flowing from said vessel and being open at its other end;
   a first transducer in the tube for continuously determining the electrical conductivity of the quantity of liquid flowing through the tube from said vessel;
   a second transducer in the tube located downstream of the first transducer for determining the specific electrical conductivity of the liquid; and
   an electronic evaluation system connected to said transducers for determining the throughflow of the liquid upon the basis of the values determined by said transducers.

2. Apparatus as claimed in claim 1, wherein the first transducer comprises two annular electrodes having inner surfaces flush with that of the tube and being spaced from each other axially thereof, the second transducer comprising a measuring chamber containing a cylindrical ring electrode having a larger, liquid inlet opening and a smaller, liquid outlet opening, and having a pin-type electrode centrally disposed therein.

3. Apparatus as claimed in claim 1, wherein said collecting vessel is in the form of a funnel, the tube extending obliquely therefrom and so having an inclined portion, said first and second transducers being located in said inclined portion and being spaced from each other axially thereof.

4. Apparatus as claimed in claim 1, wherein said collecting vessel is in the form of a funnel, the tube having an inclined portion connected to the funnel and an end portion extending at an angle with respect to said inclined portion, the first transducer being disposed in said inclined portion and the second transducer being disposed in said end portion.

5. Apparatus as claimed in claim 1, comprising a liquid laminating zone in said tube, disposed upstream of the first transducer and comprising laminating means extending axially of the tube.

6. Apparatus as claimed in claim 5, wherein said laminating means are grooves.

7. Apparatus as claimed in claim 5, wherein said laminating means are webs.

8. Apparatus as claimed in claim 1, wherein the second transducer comprises a measuring chamber having a larger, liquid inlet opening, a smaller, liquid outlet opening disposed opposite thereto, and a liquid overflow opening.

9. Apparatus as claimed in claim 1, wherein the electronic evaluation system comprises a processor connected to said transducers, and a function memory, a measured value memory and an offset memory, connected to the processor.

10. Apparatus as claimed in claim 1, wherein each of said transducers has its own power supply.

11. Apparatus as claimed in claim 1, for measuring the throughflow of urine in urological function diagnostics, wherein said vessel and said tube are adapted to be suspended in a WC bowl.

* * * * *